United States Patent
Berben et al.

(10) Patent No.: US 9,828,216 B2
(45) Date of Patent: Nov. 28, 2017

(54) CONNECTOR FOR INSPECTION SYSTEM OF ELEVATOR TENSION MEMBER

(71) Applicant: Otis Elevator Company, Farmington, CT (US)

(72) Inventors: Ruth Berben, Albany, NY (US); Richard N. Fargo, Plainville, CT (US); Peter Liaskas, Norwalk, CT (US)

(73) Assignee: OTIS ELEVATOR COMPANY, Farmington, CT (US)

( * ) Notice: Subject to any disclaimer, the term of this patent is extended or adjusted under 35 U.S.C. 154(b) by 0 days.

(21) Appl. No.: 15/119,463

(22) PCT Filed: Feb. 18, 2014

(86) PCT No.: PCT/US2014/016863
§ 371 (c)(1),
(2) Date: Aug. 17, 2016

(87) PCT Pub. No.: WO2015/126358
PCT Pub. Date: Aug. 27, 2015

(65) Prior Publication Data
US 2017/0008735 A1 Jan. 12, 2017

(51) Int. Cl.
*B66B 3/00* (2006.01)
*B66B 7/12* (2006.01)
(Continued)

(52) U.S. Cl.
CPC .......... *B66B 7/1223* (2013.01); *B66B 5/0031* (2013.01); *G01N 27/041* (2013.01)

(58) Field of Classification Search
USPC ........................................................ 187/393
See application file for complete search history.

(56) References Cited

U.S. PATENT DOCUMENTS

| 4,434,873 A | * | 3/1984 | Ohta | B66B 15/04 187/277 |
| 5,834,942 A | * | 11/1998 | De Angelis | D07B 1/025 187/226 |

(Continued)

FOREIGN PATENT DOCUMENTS

| DE | 19626284 A1 | 1/1998 |
| JP | 08194395 A | 7/1996 |

(Continued)

OTHER PUBLICATIONS

Notification of Transmittal of the International Search Report and the Written Opinion of the International Searching Authority, or the Declaration; Application No. PCT/US2014/016863; dated Nov. 13, 2014; 11 pages.

(Continued)

*Primary Examiner* — Christopher Uhlir
(74) *Attorney, Agent, or Firm* — Cantor Colburn LLP

(57) ABSTRACT

An electrical inspection system for an elevator load bearing member includes an electrically conductive, low resistance wrap located at the load bearing member, contacting the load bearing member around a circumference of the load bearing member. An inspection unit is configured to apply an electrical current through the load bearing member and determine an electrical resistance of the load bearing member, and is electrically connected to the load bearing member at the wrap to distribute electrical current uniformly therethrough. A method of determining an electrical resistance of a load bearing member of an elevator system includes applying an electrically conductive low electrical resistance wrap entirely around a circumference of the load bearing member. An inspection unit is connected to the load bearing member at the wrap. An electrical current is applied through (Continued)

the wrap into the load bearing member to determine an electrical resistance of the load bearing member.

15 Claims, 5 Drawing Sheets

(51) Int. Cl.
 *B66B 5/00* (2006.01)
 *G01N 27/04* (2006.01)

(56) References Cited

U.S. PATENT DOCUMENTS

| | | | | |
|---|---|---|---|---|
| 6,633,159 | B1* | 10/2003 | Robar | B66B 7/1223 187/391 |
| 6,653,943 | B2* | 11/2003 | Lamb | B66B 7/1223 324/513 |
| 7,123,030 | B2* | 10/2006 | Robar | B66B 7/1223 187/393 |
| 8,686,747 | B2* | 4/2014 | Berner | B66B 7/1223 187/391 |
| 8,807,286 | B2* | 8/2014 | Puranen | B66B 5/0018 187/391 |
| 2003/0011483 | A1 | 1/2003 | Lamb | |
| 2007/0173104 | A1 | 7/2007 | Veronesi et al. | |
| 2008/0148704 | A1* | 6/2008 | Angelis | D07B 1/025 57/251 |

FOREIGN PATENT DOCUMENTS

| | | |
|---|---|---|
| JP | 2001072383 A | 3/2001 |
| JP | 2009143678 A | 7/2009 |
| JP | 2013083697 A | 5/2013 |

OTHER PUBLICATIONS

EP Extended Search Report; Application No. EP 14883370.0; Dated Sep. 25, 2017; 5 pages.

* cited by examiner

CONNECTOR FOR INSPECTION SYSTEM OF ELEVATOR TENSION MEMBER

CROSS REFERENCE TO RELATED APPLICATIONS

This application is a National Phases Application of Patent Application PCT/US2014/016863 filed on Feb. 18, 2014, the entire contents of this application is incorporated herein by reference.

BACKGROUND OF THE INVENTION

The subject matter disclosed herein relates to tension members such as those used in elevator systems for suspension and/or driving of the elevator car and/or counterweight. More specifically the subject disclosure relates to systems for monitoring a tension member for wear and/or failure.

Elevator systems often include a car and a counterweight that are suspended in a hoistway via a load bearing member, such as a rope or belt. A drive machine moves the load bearing member to cause the selected movement of the car to different levels of a building. Conventional elevator systems use rope formed from steel wires as a lifting tension load bearing member. Other systems utilize a lifting belt formed from a number of steel cords, formed from steel wires, retained in an elastomeric jacket. The cords act as the load supporting tension member, while the elastomeric jacket holds the cords in a stable position relative to each other, and provides a frictional load path to provide traction for driving the belt.

During normal elevator operation, the load bearing members are subjected to a large number of bending cycles as they travel over drive sheaves and deflector sheaves of the elevator system. These bending cycles cause a degradation of the breaking strength of the ropes or cords within the coated steel belt via the mechanism of wire fretting or fatigue. Such fatigue is a major contributor to reduction in service life of the load bearing member. It is often desired to inspect the condition of the load bearing member for damage or degradation. This is done via visual inspection where practicable, but in many instances visual inspection is not possible or is insufficient, alternative methods are utilized.

Some electrical characteristics, such as electrical resistance or impedance of the rope or cords will vary with decreasing cross-section thereof. Accordingly, it is possible to determine the remaining support strength of the load bearing member based on the measured electrical characteristics. One system utilizing electrical characteristics of the rope or cords is called resistance-based inspection (RBI). An RBI system is secured to the rope or cords and monitors an electrical resistance of each cord in the belt. Since the electrical resistance of the rope or cord is proportional to its cross-sectional area, changes is electrical resistance can be correlated to reduction in cross-sectional area of the rope or cord, indicating an amount of fretting, and a corresponding remaining service life.

In a typical system, circuit leads are connected directly to the rope or cord. Direct connections, however, often result in point contact, or contacting, for example, only one or more strands of the rope while not contacting other strands at all. This results in inaccurate and non repeatable measurements.

BRIEF DESCRIPTION OF THE INVENTION

In one embodiment, an electrical inspection system for an elevator load bearing member includes an electrically conductive, low resistance wrap located at the load bearing member. The wrap uniformly contacts the load bearing member around a circumference of the load bearing member. An inspection unit is configured to apply an electrical current through the load bearing member and determine an electrical resistance of the load bearing member. The inspection unit is electrically connected to the load bearing member at the wrap to distribute electrical current uniformly through the load bearing member.

Alternatively or additionally, in this or other embodiments the wrap is secured to the load bearing member.

Alternatively or additionally, in this or other embodiments the wrap is secured to the load bearing member by one of a tie or a washer.

Alternatively or additionally, in this or other embodiments the wrap is formed from a copper material.

Alternatively or additionally, in this or other embodiments the load bearing member is a rope formed from a plurality of metallic wires.

Alternatively or additionally, in this or other embodiments the plurality of wires are twisted into a plurality of strands thereby forming the rope.

Alternatively or additionally, in this or other embodiments the wrap extends along a length of the rope equal to at least one strand lay length of the rope.

In another embodiment, a method of determining an electrical resistance of a load bearing member of an elevator system includes applying an electrically conductive low electrical resistance wrap entirely around a circumference of the load bearing member. An inspection unit is connected to the load bearing member at the wrap. An electrical current is applied through the wrap into the load bearing member. An electrical resistance of the load bearing member is determined via the inspection unit.

Alternatively or additionally, in this or other embodiments the wrap is secured to the load bearing member.

Alternatively or additionally, in this or other embodiments the wrap is secured to the load bearing member via one or more of a tie or a washer.

Alternatively or additionally, in this or other embodiments the measured electrical resistance is compared to a previous measured electrical resistance.

Alternatively or additionally, in this or other embodiments a change in the electrical resistance is indicative of wear of the load bearing member.

Alternatively or additionally, in this or other embodiments the wrap is formed from a copper material.

Alternatively or additionally, in this or other embodiments the load bearing member is a rope formed from a plurality of metallic wires.

Alternatively or additionally, in this or other embodiments the plurality of wires are arranged in a plurality of strands, the wrap extending along a length of the rope equal to at least one strand lay length of the rope.

The detailed description explains the invention, together with advantages and features, by way of examples with reference to the drawings.

DETAILED DESCRIPTION OF THE INVENTION

Figure 1A:
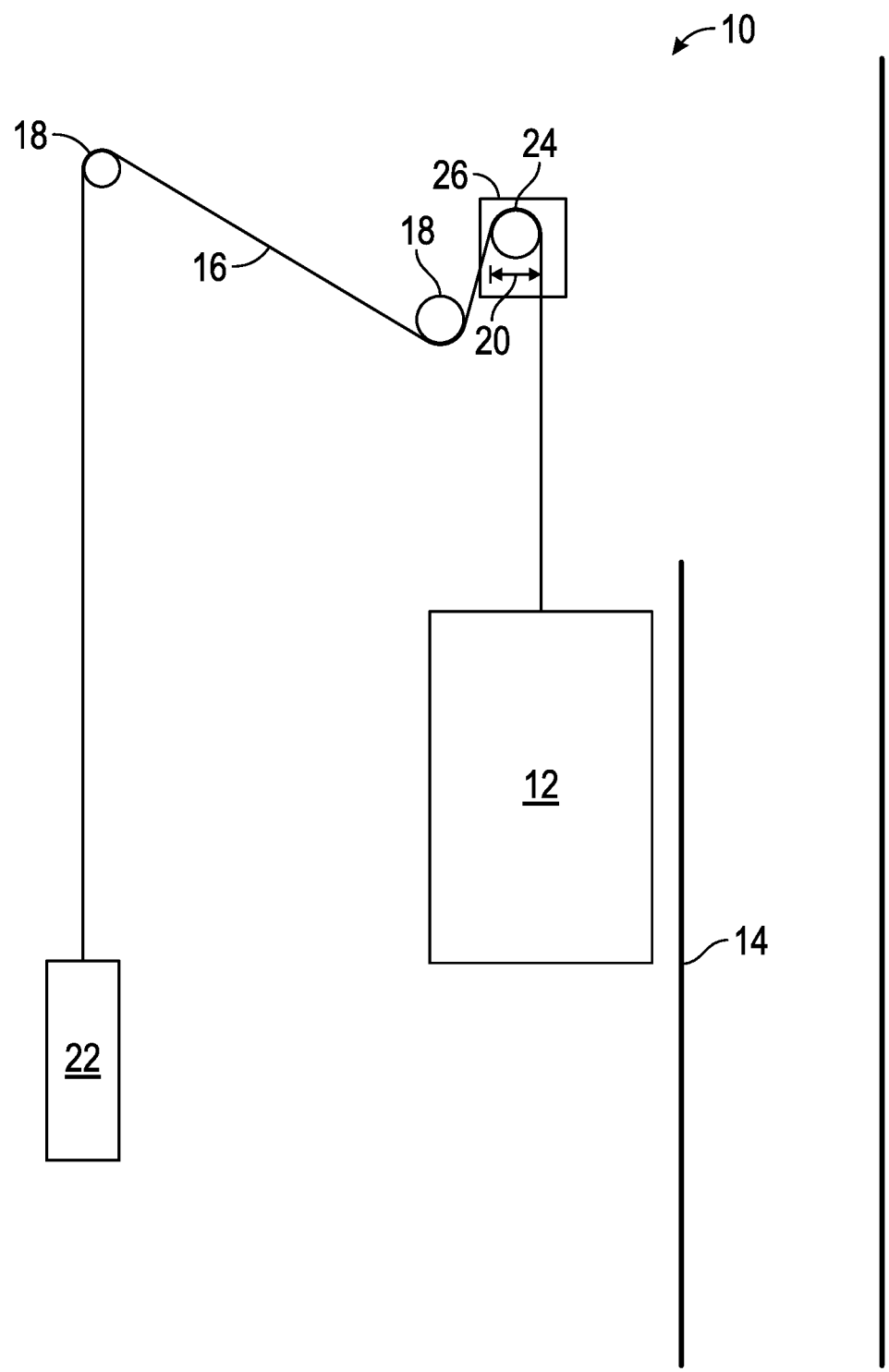
FIG. 1A is a schematic of an exemplary elevator system having a 1:1 roping arrangement.
Figure 1B:
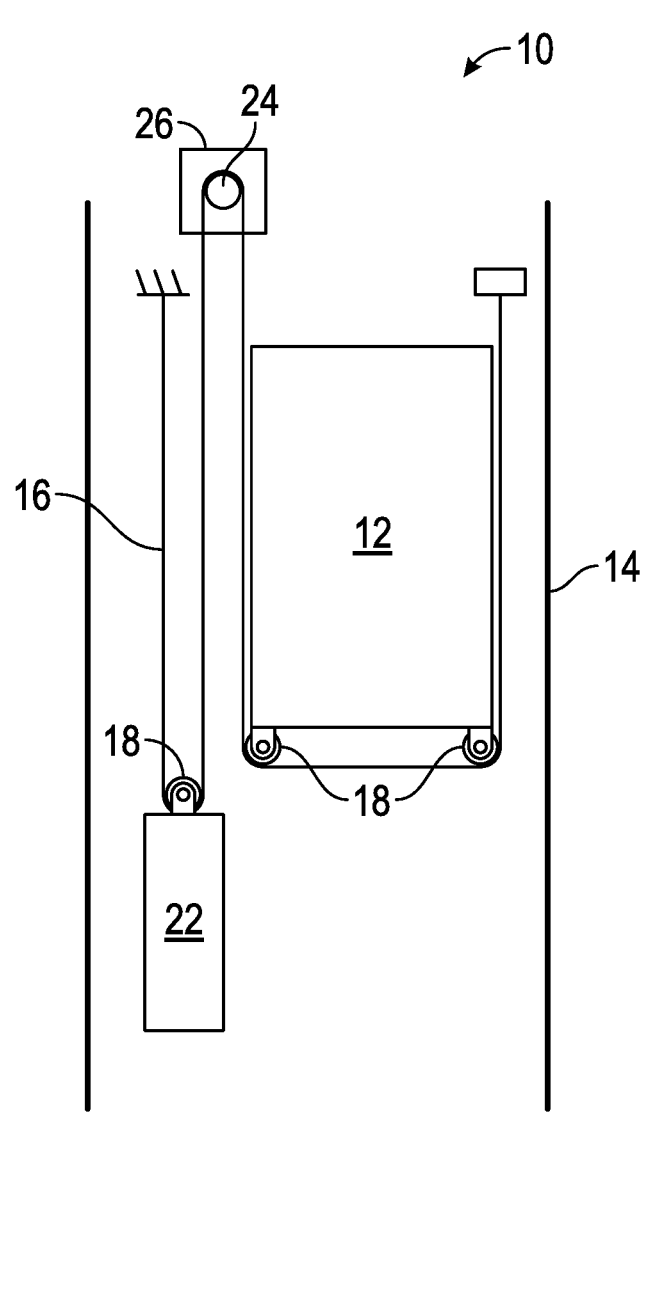
FIG. 1B is a schematic of another exemplary elevator system having a different roping arrangement.
Figure 1C:
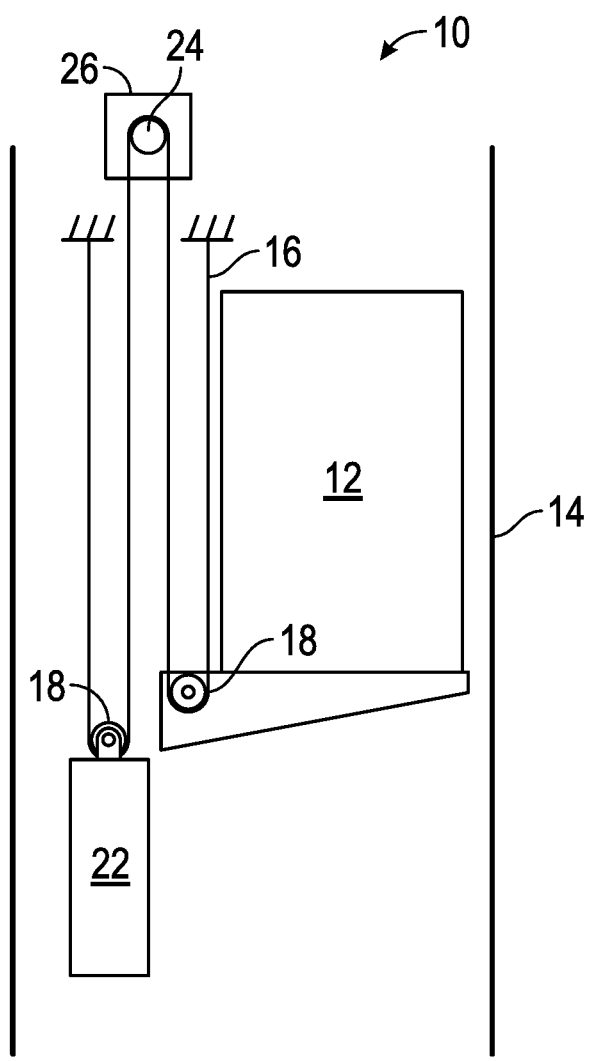
FIG. 1C is a schematic of another exemplary elevator system having a cantilevered arrangement.

Shown in FIGS. 1A, 1B and 1C are schematics of exemplary traction elevator systems 10. Features of the elevator system 10 that are not required for an understanding of the present invention (such as the guide rails, safeties, etc.) are not discussed herein. The elevator system 10 includes an elevator car 12 operatively suspended or supported in a hoistway 14 with one or more tension members, ropes 16. The one or more ropes 16 interact with one or more sheaves 18 to be routed around various components of the elevator system 10. The one or more ropes 16 could also be connected to a counterweight 22, which is used to help balance the elevator system 10 and reduce the difference in rope tension on both sides of the traction sheave during operation.

The sheaves 18 each have a diameter 20, which may be the same or different than the diameters of the other sheaves 18 in the elevator system 10. At least one of the sheaves could be a traction sheave 24. The traction sheave 24 is driven by a machine 26. Movement of the traction sheave 24 by the machine 26 drives, moves and/or propels (through traction) the one or more ropes 16 that are routed around the traction sheave 24.

At least one of the sheaves 18 could be a diverter, deflector or idler sheave. Diverter, deflector or idler sheaves are not driven by the machine 26, but help guide the one or more ropes 16 around the various components of the elevator system 10.

In some embodiments, the elevator system 10 could use two or more ropes 16 for suspending and/or driving the elevator car 12. In addition, the elevator system 10 could have various configurations such that either both sides of the one or more ropes 16 engage the one or more sheaves 18 (such as shown in the exemplary elevator systems in FIG. 1A, 1B or 1C) or only one side of the one or more ropes 16 engages the one or more sheaves 18.

FIG. 1A provides a 1:1 roping arrangement in which the one or more ropes 16 terminate at the car 12 and counterweight 22. FIGS. 1B and 1C provide different roping arrangements. Specifically, FIGS. 1B and 1C show that the car 12 and/or the counterweight 22 can have one or more sheaves 18 thereon engaging the one or more belts 16 and the one or more ropes 16 can terminate elsewhere, typically at a structure within the hoistway 14 (such as for a machineroomless elevator system) or within the machine room (for elevator systems utilizing a machine room. The number of sheaves 18 used in the arrangement determines the specific roping ratio (e.g. the 2:1 roping ratio shown in FIGS. 1B and 1C or a different ratio). FIG. 1C also provides a so-called rucksack or cantilevered type elevator. The present invention could be used on elevator systems other than the exemplary types shown in FIGS. 1A, 1B and 1C.

Figure 2:
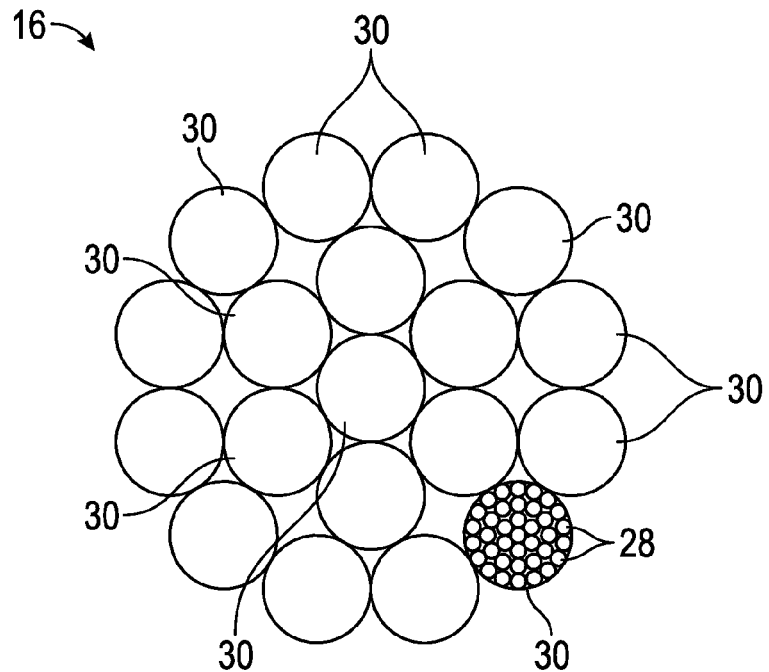
FIG. 2 is a cross-sectional view of an embodiment of an elevator rope.

FIG. 2 provides a schematic of an exemplary rope 16 construction or design. The rope 16 includes a plurality of tension elements, such as wires 28. The wires 28 are arranged into a plurality of strands 30, which are arranged to form the rope 16. The strands 30 are twisted together with a rope lay length defined by a rope 16 length in which a strand 30 makes a complete spiral around the rope 16. Similarly, the wires 28 are twisted to form each strand 30 with a strand lay length defined by a strand 30 length in which a wire 28 makes a complete spiral around the strand 30. In some embodiments, the rope 16 has a circular cross-section. It is desired to periodically inspect the rope 16 for degradation and/or damage.

Figure 3:
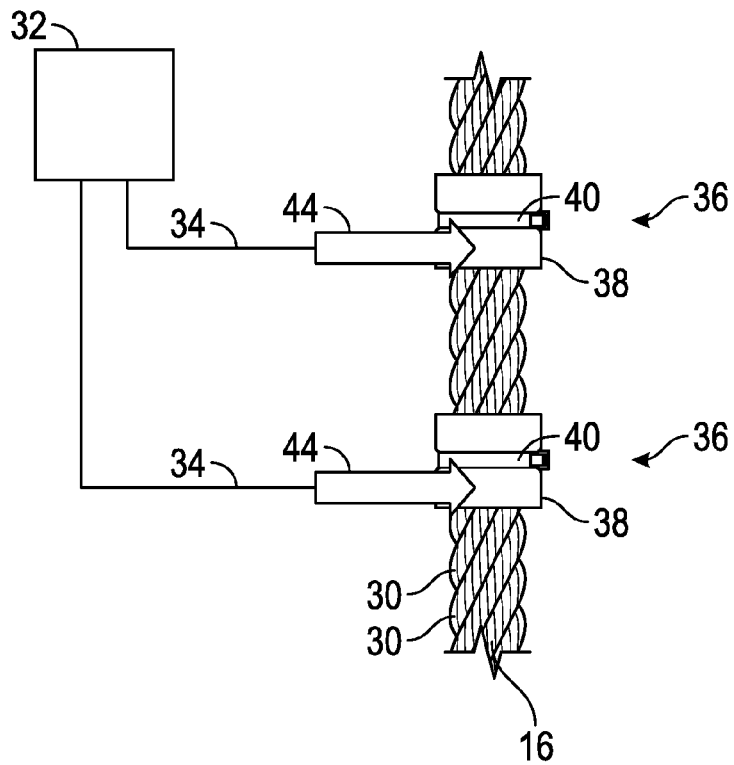
FIG. 3 is a schematic view of an embodiment of an elevator rope inspection system.

To do so, it is connected to an electrical resistance-based inspection (RBI) unit 32, an example of which is shown in FIG. 3. The RBI unit 32 is electrically connected to the rope 16. The RBI unit 32 is electrically connected to the rope 16 by one or more leads 34. During operation, an electrical current is applied through the rope 16. A resulting voltage allows for determination of an electrical resistance of the rope 16 by the RBI unit 32. This measured resistance is compared to an initial resistance of the rope 16. A change in the electrical resistance of the rope 16, typically an increase in resistance, indicates wear of the rope 16. The change in resistance is compared to a threshold change value by the RBI unit 32, and when the threshold change value is exceeded, action may be taken by the elevator system 10, including but not limited to, sounding of an alarm or stopping operation of the elevator system 10.

To ensure accuracy and repeatability of the measured resistance, a connector 36 is secured to the rope 16 to facilitate uniform connection of the leads 34 to the rope 16. The connector 36 is formed from a low resistive, conductive wrap 38 extending entirely around a circumference of the rope 16 located at a portion of the rope 16 length. The material is chosen to be low resistive so that the wrap 38 will not effect the magnitude of the resistance measurement, and in some embodiments is a copper material. The wrap 38 is secured to the rope 16 to provide continuous contact between the wrap 38 and the rope 16 entirely around the circumference of the rope 16. Further, in some embodiments, the wrap 38 extends along the length of the rope 16, for at least one full strand lay length of the wires 28 in a strand 30. As such, the wrap 38 will then contact all of the external wires 28 in every external strand 30, which eliminates the wire to wire resistance, improving accuracy at least for external wires 28.

Figure 4:
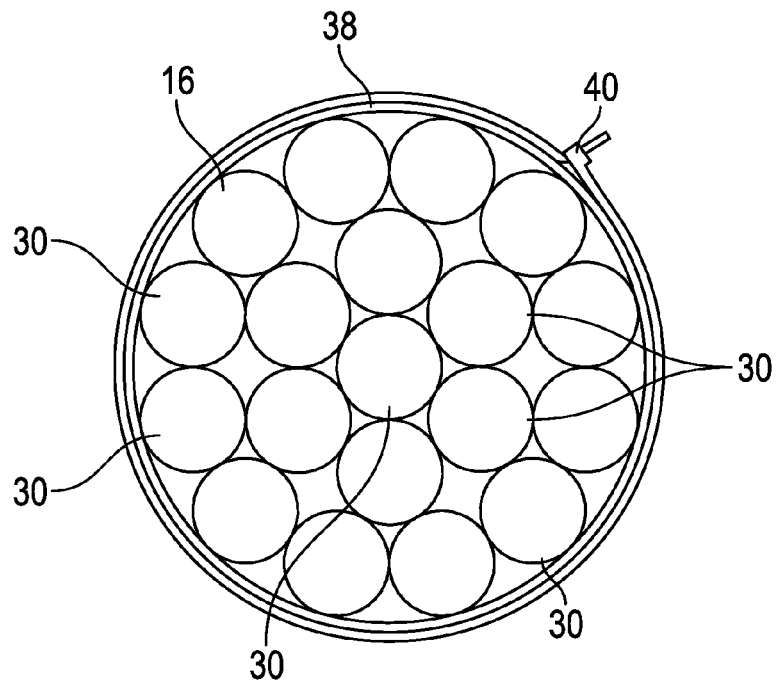
FIG. 4 is a cross-sectional view of another embodiment of an elevator rope.
Figure 5:
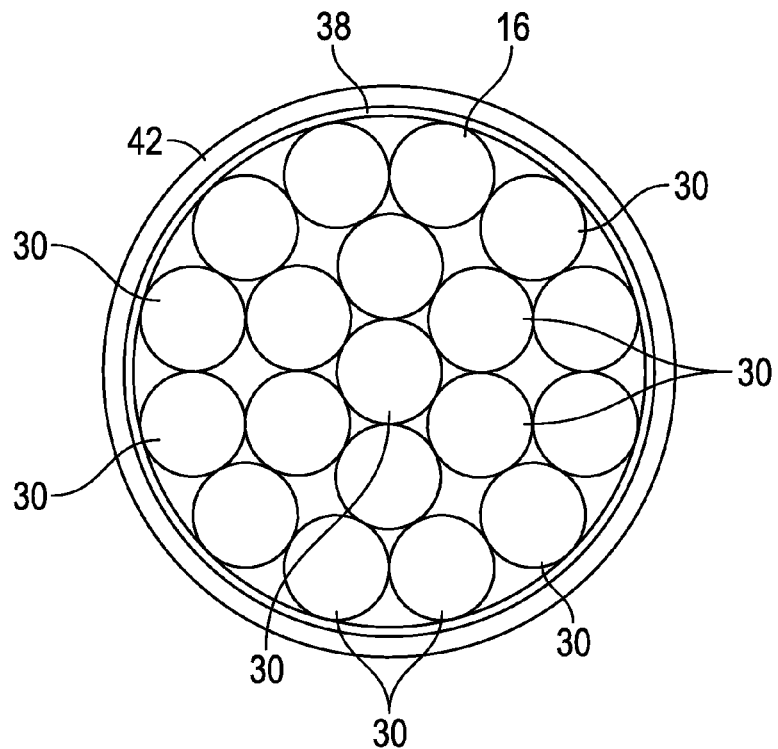
FIG. 5 is a cross-sectional view of yet another embodiment of an elevator rope.

In some embodiments, as shown in FIGS. 4 and 5, the wrap is secured by a tie 40, such as a zip tie, or alternatively by a clamp 42, such as a hose clamp placed over the rope 16. It is to be appreciated that these are merely examples, and other means may be used to secure the wrap 38 to the rope 16. Referring again to FIG. 3, the lead 34 is then connected to the wrap 38 by, for example a clip 44. The lead 34 is thereby connected, via the wrap 38, entirely around the circumference of the rope 16, such that the electrical current is applied uniformly through each strand 30 or wire 28 of the rope 16. The uniform application of current allows for accurate and repeatable measurement of the total rope 16 resistance.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. An electrical inspection system for an elevator load bearing member comprising:
    an electrically conductive, low resistance wrap disposed at the load bearing member, and uniformly contacting the load bearing member around a circumference of the load bearing member; and
    an inspection unit configured to apply an electrical current through the load bearing member and determine an electrical resistance of the load bearing member;
    wherein the inspection unit is electrically connected to the load bearing member at the wrap to distribute electrical current uniformly through the load bearing member.

2. The inspection system of claim 1, wherein the wrap is secured to the load bearing member.

3. The inspection system of claim 2, wherein the wrap is secured to the load bearing member by one of a tie or a clamp.

4. The inspection system of claim 1, wherein the wrap is formed from a copper material.

5. The inspection system of any of claim 1, wherein the load bearing member is a rope formed from a plurality of metallic wires.

6. The inspection system of claim 5, wherein the plurality of wires are twisted into a plurality of strands thereby forming the rope.

7. The inspection system of claim 6, wherein the wrap extends along a length of the rope equal to at least one strand lay length of the rope.

8. A method of determining an electrical resistance of a load bearing member of an elevator system comprising:
    applying an electrically conductive low electrical resistance wrap entirely around a circumference of the load bearing member;
    connecting an inspection unit to the load bearing member at the wrap;
    applying an electrical current through the wrap into the load bearing member; and
    determining an electrical resistance of the load bearing member via the inspection unit.

9. The method of claim 8, further comprising securing the wrap to the load bearing member.

10. The method of claim 8, further comprising securing the wrap to the load bearing member via one or more of a tie or a clamp.

11. The method of claim 8, further comprising comparing the determined electrical resistance to a previous determined electrical resistance.

12. The method of claim 11, wherein a change in the electrical resistance is indicative of wear of the load bearing member.

13. The method of claim 8, wherein the wrap is formed from a copper material.

14. The method of claim 8, wherein the load bearing member is a rope formed from a plurality of metallic wires.

15. The method of claim 14, wherein the plurality of wires are arranged in a plurality of strands, the wrap extending along a length of the rope equal to at least one strand lay length of the rope.

* * * * *